US012622798B2

(12) United States Patent　　　　　(10) Patent No.:　　US 12,622,798 B2
Park　　　　　　　　　　　　　　　　　(45) Date of Patent:　　　May 12, 2026

(54) ORTHOTIC DEVICE FOR CONTROLLING FOOT MOTION

(71) Applicant: James F. Park, Park City, UT (US)

(72) Inventor: James F. Park, Park City, UT (US)

( * ) Notice: Subject to any disclaimer, the term of this patent is extended or adjusted under 35 U.S.C. 154(b) by 264 days.

(21) Appl. No.: 18/589,292

(22) Filed: Feb. 27, 2024

(65) Prior Publication Data

US 2024/0285422 A1　　　Aug. 29, 2024

Related U.S. Application Data

(60) Provisional application No. 63/448,493, filed on Feb. 27, 2023.

(51) Int. Cl.
A61F 5/01　　　　　(2006.01)
(52) U.S. Cl.
CPC ................................. A61F 5/0113 (2013.01)
(58) Field of Classification Search
CPC ............ A61F 5/0113; A61F 2005/0179; A61F 5/0127; A61F 5/0111; A61F 5/0104; A61F 5/0102; A61F 5/01; A61F 5/00; A61F 2005/013
See application file for complete search history.

(56) References Cited

U.S. PATENT DOCUMENTS

| 2,567,195 | A | 9/1951 | Ellery | |
| 9,398,970 | B1 * | 7/2016 | Meyer | A61F 5/0111 |
| 11,278,434 | B2 | 3/2022 | Kroll-Orywahl et al. | |
| 11,395,753 | B2 | 7/2022 | LeCursi et al. | |
| 2016/0361189 | A1 * | 12/2016 | Campbell | A61F 5/0125 |
| 2017/0231797 | A1 * | 8/2017 | LeCursi | A61F 5/0125 |
| | | | | 602/16 |
| 2022/0054291 | A1 | 2/2022 | Huber | |

FOREIGN PATENT DOCUMENTS

| FR | 3111791 | B1 | 10/2022 |
| KR | 1020200054388 | A | 5/2020 |

* cited by examiner

*Primary Examiner* — Tarla R Patel
(74) *Attorney, Agent, or Firm* — PETERSON IP; Brett Peterson

(57)　　　　　　ABSTRACT
An ankle and foot orthotic device biases the foot of a user into dorsiflexion to control drop foot and other conditions caused by neurological or muscular impairment; allowing a user to stand, walk, and participate in desired activities with greater ease and balance. The device resists rapid motions of the foot and assists the user in many aspects of walking including controlling the drop of the foot front after heel strike, stabilizing standing in a neutral position, and strengthening the ability to push off of the toes at the end of the stride.

20 Claims, 13 Drawing Sheets

ORTHOTIC DEVICE FOR CONTROLLING FOOT MOTION

PRIORITY

The present application claims the benefit of U.S. Provisional Application Ser. No. 63/448,493, filed Feb. 27, 2024, which is herein incorporated by reference in its entirety.

THE FIELD OF THE INVENTION

The present invention relates to orthotics. In particular, examples of the present invention relate to an ankle and foot orthotic device which provides increased control over foot motion and position for a person having drop foot or another neurological or muscular impairment which impedes control over the foot.

INTRODUCTION

Many individuals suffer from conditions that affect control over the foot. Conditions such as drop foot prevent a user from fully controlling the position and motion of their foot. These conditions may arise from diseases or injuries that affect the nerves of muscles. These conditions may be quite debilitating as they can affect the person's ability to walk, stand, and participate in other desired activities.

BRIEF DESCRIPTION OF THE DRAWINGS

Non-limiting and non-exhaustive examples of the present invention are described with reference to the following figures, wherein like reference numerals refer to like parts throughout the various views unless otherwise specified.

Figure 1:
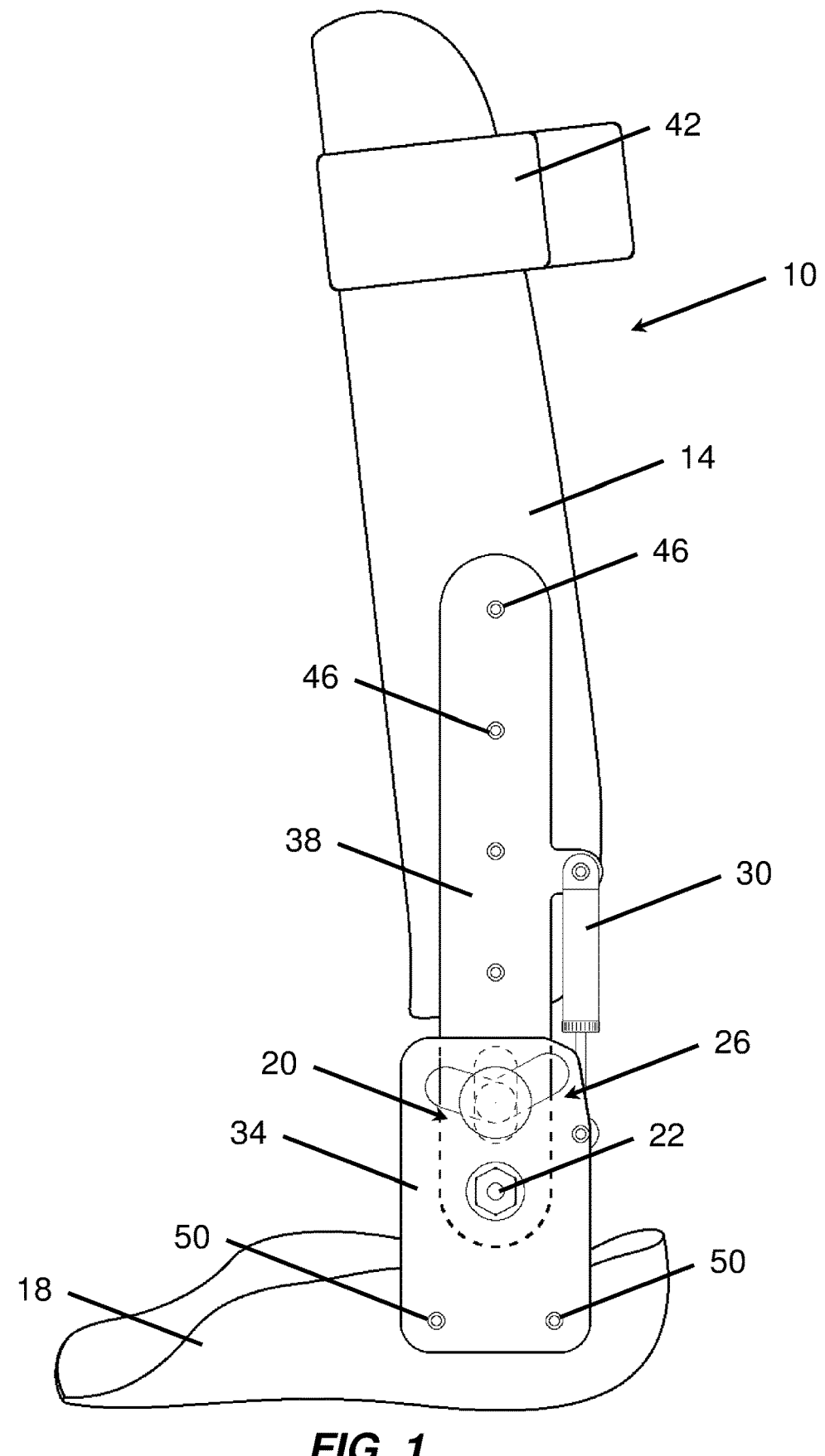
FIG. 1 is a drawing which shows a side view of an ankle and foot orthotic device.

Corresponding reference characters indicate corresponding components throughout the several views of the drawings. Unless otherwise noted, the drawings have been drawn to scale. Skilled artisans will appreciate that elements in the figures are illustrated for simplicity and clarity. For example, the dimensions of some of the elements in the figures may be exaggerated relative to other elements to help improve understanding of various examples of the present invention. Also, common but well-understood elements that are useful or necessary in a commercially feasible embodiment are often not depicted in order to facilitate a less obstructed view of these various embodiments of the present invention.

It will be appreciated that the drawings are illustrative and not limiting of the scope of the invention which is defined by the appended claims. The examples shown each accomplish various different advantages. It is appreciated that it is not possible to clearly show each element or advantage in a single figure, and as such, multiple figures are presented to separately illustrate the various details of the examples in greater clarity. Similarly, not every example need accomplish all advantages of the present disclosure.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

In the above disclosure, reference has been made to the accompanying drawings, which form a part hereof, and in which are shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, such feature, structure, or characteristic may be used in connection with other embodiments whether or not explicitly described. The particular features, structures or characteristics may be combined in any suitable combination and/or sub-combinations in one or more embodiments or examples. It is appreciated that the figures provided herewith are for explanation purposes to persons ordinarily skilled in the art.

As used herein, "adjacent" refers to near or close sufficient to achieve a desired effect. Although direct contact is common, adjacent can broadly allow for spaced apart features.

As used herein, the singular forms "a," and, "the" include plural referents unless the context clearly dictates otherwise.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be such as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a number or numerical range endpoint by providing that a given value may be "a little above" or "a little below" the number or endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Dimensions, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range.

The disclosure particularly describes an orthotic device to assist people with muscular or nerve impairment in feet. Particularly, the present disclosure describes an orthotic device which provides relief for a drop foot condition or similar conditions where a person has reduced nerve or muscular control over their foot. The device assists the person with foot control and makes walking and other daily activities easier for the person.

FIG. 1 shows a side view of an ankle and foot orthotic device 10. The ankle and foot orthotic device 10 is a mechanically active device that is designed to assist and approximate an active gait cycle for patients who have drop foot or similar neuromuscular impairments. The device simulates both the stance and swing phases of gait. During the stance phase the device lifts the foot in dorsiflexion for an in-sync heel strike and then progresses with some resistance in plantarflexion to a stable forefoot contact. During the swing phase the device lifts the foot in dorsiflexion for forefoot clearance to minimize the incidence of toe drag. The ankle and foot orthotic device 10 utilizes a combination of a control cam and follower with a biasing strut or spring to move the foot and promote normal foot and ankle motion during the gait cycle. The device is also designed to aid stability in vertical standing as well as other activities.

Many people suffer from nerve or muscle damage which affects their feet and thereby affects their ability to walk, stand, and participate in common activities in a normal manner. Inadequate muscular control of the foot allows the foot to drop downwardly when not in contact with the ground and prevents the foot from properly supporting the body while walking. Foot drop often causes the person to stumble while walking and interferes with activities where foot control is necessary. The orthotic device 10 provides additional support to the foot and controls the position of the foot while performing activities such as walking and standing.

The device assists a user in all stages of walking to achieve better controlled foot movement and increased stability. When a person has nerve or muscle impairment that affects control over their foot, they may have insufficient strength or control over their foot through the walking gait cycle. The device biases the foot in dorsiflexion to pull the toe up. This helps a user to avoid striking the front of their foot and helps them to not trip while walking. The device also slows and controls the movement of the foot. The movement of the cam follower 82 through the vertical cam slot 74 and horizontal cam slot 78 causes sufficient friction to limit fast foot movements without causing undue resistance to movement at a desired foot speed while walking. This prevents uncontrolled quick movement of the foot, such as quick movement of the front of the foot downwardly after heel strike while walking. Uncontrolled foot movement while walking often causes the front of the foot to quickly slap the ground after heel strike. The device limits the speed of foot movement and prevents uncontrolled foot slap or other undesired movements. The device also increases the user's control over their waking gait by adding resistance and slowing the motion of the foot in the downward motion of the foot after heel strike, towards a neutral standing position and through dorsiflexion as the user places weight on their toes. The device also aids the user in pushing off of the toe. The resistance to quick motion created by the cam and cam follower assists the user in pushing off with their toes. Once the user has pushed off of their toes and is not putting weight on the motion control joint, the device is able to move more quickly and assists in lifting the toes to avoid toe strike.

The orthotic device 10 includes a leg support shell 14 which is connected to a foot support 18. The example leg support 14 is a molded plastic shell that contacts the front and sides of the shin. The leg support 14 is U-shaped when viewed from above to comfortably engage the front of the lower leg. The foot support 18 is molded in a U-shape when viewed from the front and receives the foot in the opening formed by the top of the foot brace so that the user's foot contacts the top and inside of the foot brace 18. The foot brace 18 is shaped to conform to the user's foot. The foot brace 18 is connected to the leg shell 14 with a motion control joint that includes a pivot 22, a cam 26, and a biasing member such as a spring or strut 30. In the example orthotic 10, the foot brace 18 is attached to the leg shell 14 by an aluminum or metal foot control joint member 34 which may be formed from a vertically oriented plate. The foot control joint member 34 is attached to the foot brace 18. The foot control joint member 34 forms part of the motion control joint 20 and forms part of the pivot joint 22 and cam 26 and attaches to the spring strut 30. In the example orthotic 10, the leg shell 14 is attached to the foot brace 18 by an aluminum or metal leg control joint member 38 which may be formed from an elongate vertically oriented plate. The leg control joint member 38 is attached to the leg shell 14. The leg control joint member forms part of the motion control joint 20 and forms part of the pivot joint 22 and cam 26 and attaches to the spring strut 30.

The leg shell 14 may be formed from a material such as a thermoplastic, metal, or composite material that is shaped or selected to fit around the front of a user's lower leg. The leg shell 14 may be attached to the user's lower leg by one or more straps 42 which may be made from materials such as hook and loop fastener or elastic material. The shape of the leg shell 14 is selected to comfortably and securely attach to the user's lower leg and minimize motion between the leg shell 14 and the user's lower leg. The foot brace 18 may be formed from a material such as a thermoplastic, metal, or composite material and may be shaped or selected to fit the bottom of a user's foot. The foot brace 18 extends around the user's heel and forwards to a position adjacent the ball of the user's foot; terminating behind the toes to leave control of the toes to the user. The foot brace is shaped or selected to minimize motion between the foot brace and the user's foot. The leg shell 14 and foot brace 18 are selected or formed to fit snugly to the user's foot and lower leg to allow the orthotic 10 to stabilize the user's foot relative to the lower leg during use.

The pivot point 22 is fixed in location relative to both the foot brace 18 and the leg shell 14. The pivot point 22 is typically positioned in alignment with a mechanical axis of the user's ankle to allow the person to move their foot through plantarflexion or dorsiflexion without binding at the pivot point 22 or causing the foot brace 18 or leg shell 14 to move relative to the user's body. In one example, the leg control joint member 38 may be attached to the leg shell 14 by fasteners 46, allowing for easier customizing of the orthotic device 10 by selecting a desired leg shell 14 and leg control joint member 38. Similarly, the foot control joint member 34 may be attached to foot brace 18 by fasteners 50 which allow for easier customization of the orthotic device 10 by selecting a desired foot brace 18 and foot control joint member 34. Foot control joint members 34 and leg control joint members 38 may have different lengths and dimensions, different locations of the pivot joint 22, different cam slot profiles, and different lift spring/strut attachment points. Selection of a leg control joint member 38 and foot control joint member 34 allows for selection of a desired location for the pivot joint 22, selection of a desired configuration of the left spring/strut 30, and selection of a desired configuration for the cam 26. The control joint 20 allows the foot brace 18 and foot control joint member to pivot relative to the leg shell 14 and leg control joint member 38 and thereby allow the user's foot to pivot relative to the user's leg in dorsiflexion and plantarflexion while biasing the foot in dorsiflexion and providing resistance to motion.

The pivot joint 22 constrains motion of the ankle control joint to pivoting about the selected location for the pivot joint 22. The pivot joint 22 may limit lateral movement of the user's ankle and help control up and down movement of the foot through dorsiflexion and plantarflexion. The cam 26 may be tailored to provide increased stability of the ankle control joint at a certain point, such as at a neutral standing position. The cam 26 may also be tailored to provide resistance to motion. For example, the cam 26 may be designed to provide resistance to plantarflexion of the foot brace 18 and to encourage dorsiflexion of the foot brace 18. Different cam profiles may allow for increased or decreased resistance to motion in either plantarflexion or dorsiflexion or both. The spring/strut 30 is designed to bias the foot brace into a dorsiflexion motion relative to the leg shell 14 and to bias the user's foot into a position where the user's foot is elevated in dorsiflexion relative to a neutral standing position. The spring strut 30 is shown on the back side of the pivot joint 22 and provides an extension force to lift the front of the foot brace 14 in dorsiflexion. Alternatively, the spring strut 30 may be attached to the front side of the pivot joint 22 and provide a tension force to lift the front of the foot brace 14 in dorsiflexion.

Figure 2:
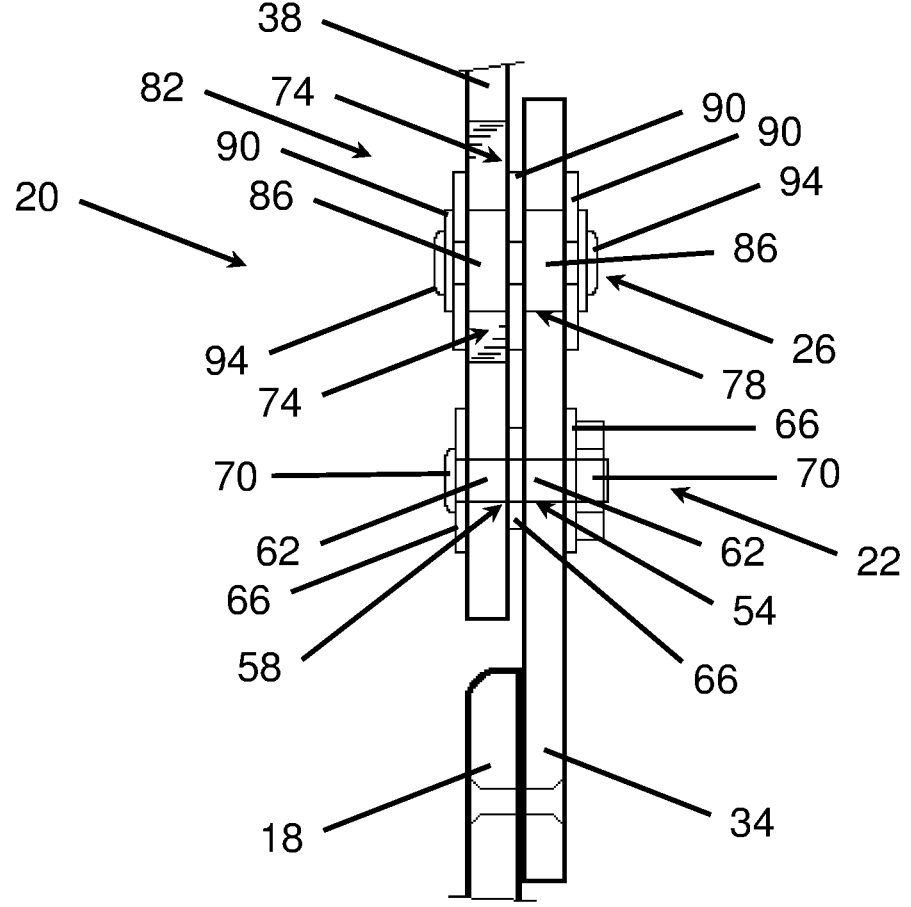
FIG. 2 is a drawing which shows a front cross-sectional view of the orthotic device control joint.

FIG. 2 shows a front side cross-sectional view of the ankle motion control joint 20. The foot control joint member 34 and leg control joint member 38 are shown. The pivot joint 22 is a joint which is constrained to allow rotational motion between the ankle control member 34 and leg control member 38 about a pivot point and inhibits other motion between the foot control joint member 34 and leg control joint member 38. The pivot joint 22 may include a first hole 54 in the foot control joint member 34 and a second hole 58 in the leg control joint member 38. The pivot joint 22 may include bearings 62 which fit in the holes 54, 58, spacers 66 (such as bushings or thrust bearings) which fit between the foot control joint member 34 and leg control joint member 38 and adjacent the outside sides of the foot control joint member 34 and the leg control joint member 38 to hold the bearings 62 in place and to reduce friction between the foot control joint member 34 and the leg control joint member 38. The pivot joint also includes a fastener 70 which forms a pivot shaft and holds the joint 22 together.

The control cam 26 includes a vertically oriented cam slot 74 formed in the leg control joint member 38 and a horizontally oriented cam profile slot 78 in the ankle control joint member 34. It will be appreciated that the vertically oriented cam slot 74 may be formed in the foot control joint member 34 and that the horizontally oriented cam profile slot 78 may be formed in the leg control joint member 38. The control cam 26 includes a cam follower 82 which moves vertically in the vertically oriented cam slot 74 and which moves horizontally and vertically in the horizontally oriented cam profile slot 78 when the foot control joint member 34 is pivoted relative to the leg control joint member 38. The cam follower 82 includes bearings 86 disposed in the vertically oriented cam slot 74 and in the horizontally oriented cam profile slot 78, guide spacers 90 (such as bushings or thrust bearings) disposed between and on the outer sides of the foot control joint member 34 and the leg control joint member 38, and a fastener 94 which passes through the guide spacers 90 and bearings 86 and holds the control cam 26 together. The vertically oriented cam slot 74 and the horizontally oriented cam profile slot 78 have a small amount of clearance around the bearings 86 so that the bearings 86 cam move through the slots without binding and the outer shell of the bearings may rotate to minimize binding as the cam follower 82 moves through the cam slots 74, 78.

Figure 3A:
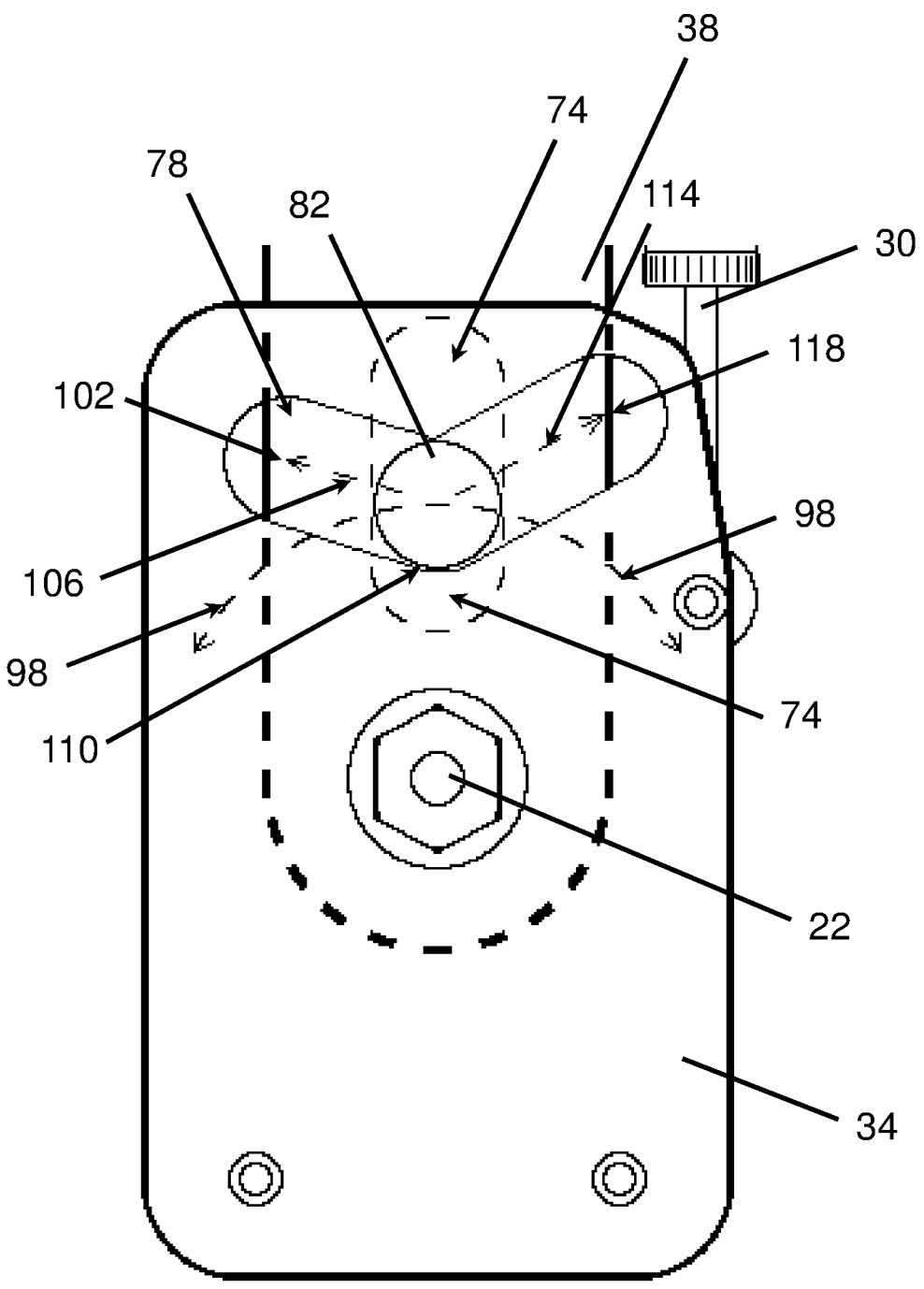
FIG. 3A shows a detailed side view drawing of the orthotic device control joint.

FIG. 3A shows a detailed side view of the ankle motion control joint 20. The cam mechanism 26 is particularly detailed, showing the shape of the horizontally oriented cam profile slot 78 in the ankle control joint member 38 and the vertically oriented cam slot 74 in the leg control joint member 38. The cam follower 82 is shown in a simplified form to allow greater visibility in showing the cam slots and joint movement. As discussed, the foot control joint member 34 pivots relative to the leg control joint member 38 about the pivot joint 22. If the cam follower 82 were to remain in a stationary position relative to the ankle control joint member 34, it would move in the arc 98 relative to the ankle control joint member 34. In other words, the arc 98 shows the shape of a horizontal cam profile slot 78 which would allow the foot control joint member 34 to pivot without requiring the cam follower 82 to move vertically in the vertical cam slot 74. The leg control joint member 38 includes a vertically oriented cam slot 74 which allows the cam follower 82 to move vertically relative to the leg control joint member 38 within the vertical cam slot 74. The foot control joint member 34 includes a generally horizontal cam profile slot 78 which deviates from an arc 98 about the pivot joint 22. The horizontal cam slot 78 does not follow the arc 98 which would allow the cam follower 82 to remain stationary relative to the leg control joint member 38. The horizontal cam profile slot 78 deviates from the arc 98 to cause the cam follower to move vertically within the vertical cam slot 74 relative to the leg control joint member 38. The horizontal cam slot 78 is typically not perfectly horizontal and is generally not straight, but is generally horizontal in orientation and is generally transverse to the vertically oriented cam slot 74.

The horizontal cam slot 78 includes a dorsiflexion end stop 102, a dorsiflexion travel zone 106, a neutral position 110, a plantarflexion travel zone 114, and a plantarflexion end stop 118. The dorsiflexion end stop 102 and plantarflexion end stop 118 are typically a semi-circular or rounded end of the horizontal cam slot 78 where the cam follower 82 contacts the end of the cam slot to prevent further rotation of the foot motion control member 34 relative to the leg motion control member 38. The horizontal cam slot 78 may have the dorsiflexion end stop 102 and the plantarflexion end stop 118 positioned to limit the movement of the foot motion control member 34 to a desired angular range of motion. In one example the foot control member 34 may be allowed to move from a neutral standing position between about 10 and about 20 degrees in dorsiflexion or by about 20 degrees or about 15 degrees in dorsiflexion. In one example the foot control member 34 may be allowed to move from a neutral standing position between about 20 and about 35 degrees in plantarflexion or by about 25 degrees or about 30 degrees in plantarflexion. The dorsiflexion travel zone 106 and the plantarflexion travel zone 114 are typically angled relative to arc 98 such that the cam follower 82 is forced to move vertically within the vertically oriented cam slot 74 during plantarflexion or dorsiflexion of the foot brace 18 relative to the leg shell 14. As discussed herein, a negative slope for a cam travel zone 106, 114 means that the cam travel zone slopes towards the pivot point 22 relative to arc 98 and allows the cam follower 82 to move downwardly within the vertically oriented cam slot 74 towards the pivot point 22 as the foot control joint member 34 pivots away from a neutral position 110. A positive slope for a cam travel zone 106, 114 means that the cam travel zone slopes away from the pivot point 22 relative to the arc 98 and requires the cam follower 82 to move vertically away from the pivot point 22 within the vertically oriented cam slot 74 as the foot control joint member 34 pivots away from a neutral position.

For the orthotic device 10, the cam neutral position is a neutral standing position which places the foot (foot control joint member 34) close to perpendicular to the leg (leg control joint member 38). The neutral position 110 of the horizontal cam slot 78 may include a small detent which allows a small upward or downward movement of the cam follower 82 at the neutral position. The neutral position detent may include as a small section where the horizontal cam slot is closer to the pivot point 22 or where the dorsiflexion travel zone 106 and plantarflexion travel zone 114 have positive slope away from the neutral position. Correspondingly, a small upward movement of the cam follower 82 is required to pivot the foot brace 18 and foot control joint member 34 away from the neutral position. The dorsiflexion travel zone 106 is typically formed with a slope away from the neutral position that is between about −5 degrees or −10 and about 10 degrees or about 30 degrees. In the example orthotic device 10, the dorsiflexion travel zone 106 has a slope away from the neutral position which is about 30 degrees. The dorsiflexion travel zone slope, combined with the lift spring or strut 30, biases the foot brace 18 towards dorsiflexion.

In viewing the dorsiflexion travel zone 106, it can be seen how the angular difference between the center line of the travel zone 106 and the neutral arc 98 increases with increasing distance away from the neutral position 110. As the foot control joint member 34 is rotated clockwise in dorsiflexion, the slope of the travel zone 106 increases relative to the vertical cam slot 74 and the cam follower 82 moves an increasing distance vertically per degree of rotation of the foot control joint member 34. The dorsiflexion travel zone 106 begins with an effective slope near the neutral position 110 that is about 25 degrees and ends with an effective slope near the dorsiflexion end stop 102 that is about 45 degrees (for about 20 degrees of rotation of the foot control joint member 34).

The plantarflexion travel zone 114 is typically formed with a positive slope away from the neutral position that is between about 10 degrees and about 50 degrees. In the example orthotic device 10, the plantarflexion travel zone 114 has a slope away from the neutral position which is about 40 degrees. The plantarflexion travel zone 114 begins with an effective slope near the neutral position 110 that is about 40 degrees and ends with an effective slope near the plantarflexion end stop 118 that is about 65 degrees (for about 25 degrees of rotation of the foot control joint member 34). Typically, the plantarflexion travel zone 114 has a slope which is greater (more positive) than the slope of the dorsiflexion travel zone 106. The plantarflexion travel zone slope, combined with the lift spring 30, biases the foot brace 18 against from plantarflexion and towards a neutral position and typically towards toe lift. The orthotic device 10 provides a stronger bias to move the foot from toes extended or pointed towards a neutral position and a weaker bias to move the foot from the neutral position towards having the toes lifted.

It will be appreciated that the cam 26 may alternatively be configured with the vertically oriented cam slot 74 in the foot control joint member 34 and the horizontally oriented cam slot 78 in the leg control joint member 38 with a forwards/backwards reversal of the horizontally oriented cam slot 78 so that the dorsiflexion travel zone 106 is extending towards the back (heel side) of the leg control joint member 38 and the plantarflexion travel zone 110 extending towards the front (toe side) of the leg control joint member 38 to retain the functionality discussed above. FIG. 3F shows such a configuration with the reversed horizontal cam slot 78 in the leg control joint member 38 and the vertical cam slot 74 in the foot control joint member 34.

Figure 3B:
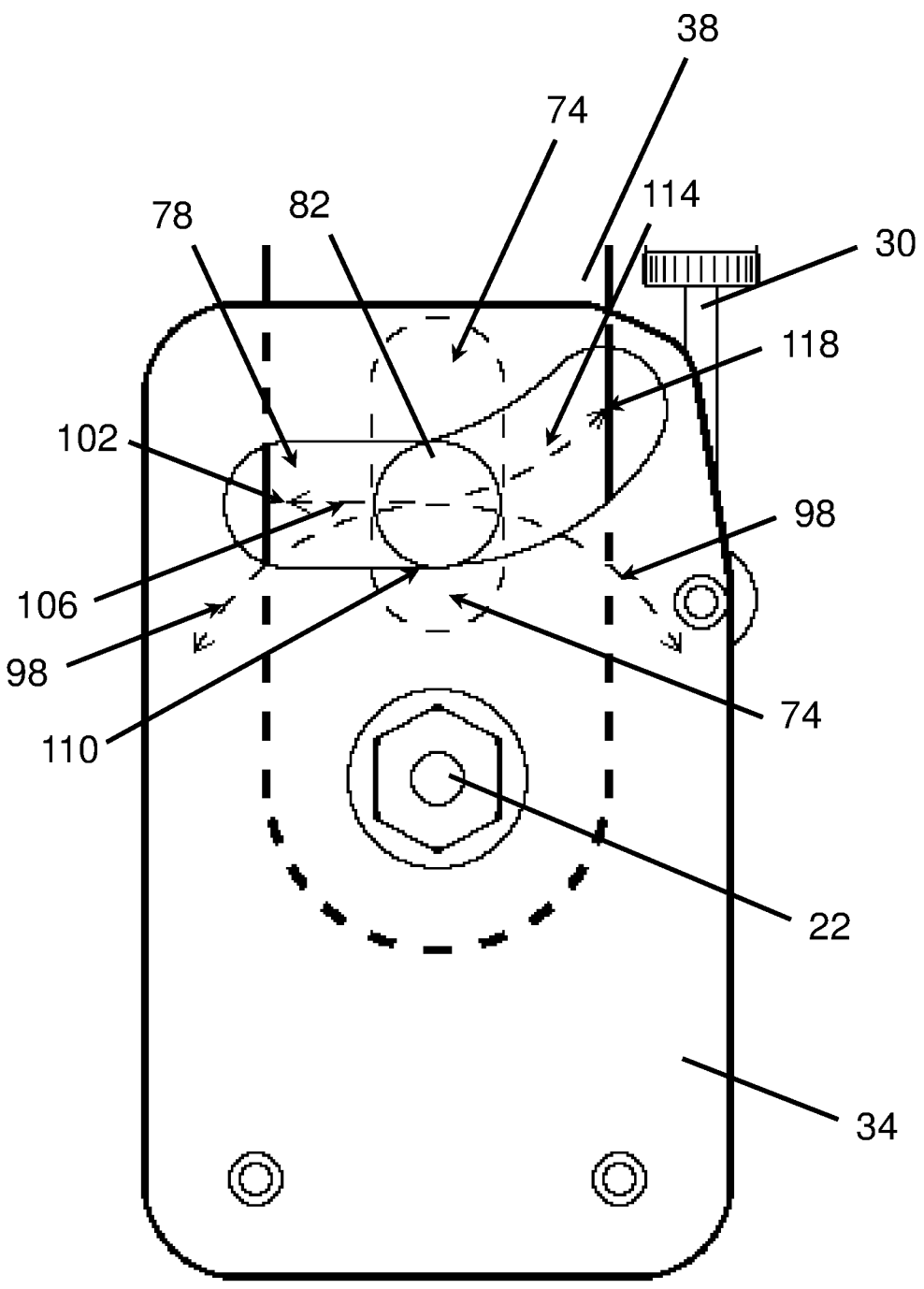
FIG. 3B shows another detailed side view drawing of the control joint.

FIG. 3B shows another detailed side view of the ankle motion control joint 20. The control joint 20 is the same as is shown in FIG. 3A except that the cam mechanism 26 has a differently shaped horizontal cam profile slot 78. The horizontal cam slot 78 includes a dorsiflexion end stop 102, a dorsiflexion travel zone 106, a neutral position 110, a plantarflexion travel zone 114, and a plantarflexion end stop 118. Compared to the horizontal cam profile slot shown in FIG. 3A, the dorsiflexion travel zone 106 maintains a positive slope and is less steeply sloped away from the neutral position 110. Compared to the horizontal cam profile slot 78 of FIG. 3A, the plantarflexion travel zone 114 has a curved travel path which begins less steeply sloped near the neutral position 110 (about 30 degrees slope) and which curves to increase in slope to a greater degree than a straight travel zone (about 70 degrees slope).

The neutral position 110 of the horizontal cam slot 78 includes a detent position which is less defined than that of FIG. 3A. Where the cam profile slot of FIG. 3A changes slope abruptly between the dorsiflexion travel zone 106 and the plantarflexion travel zone 114 at the neutral position 110, this neutral position 110 is characterized by a continuous transition between the dorsiflexion travel zone 106 and the plantarflexion travel zone 114. The horizontal cam profile slot 78 still provides a local minimum for the cam follower 82 at the neutral position 110, but does so with smaller travel and smoother change of travel direction near the neutral position 110. A small upward movement of the cam follower 82 is still required to pivot the foot brace 18 and foot control joint member 34 away from the neutral position. Compared to the cam profile slot of FIG. 3A, the cam profile slot 78 provides a stronger bias to move the foot from toes extended or pointed towards a neutral position and a stronger bias to move the foot from the neutral position and towards having the toes lifted.

Figure 3C:
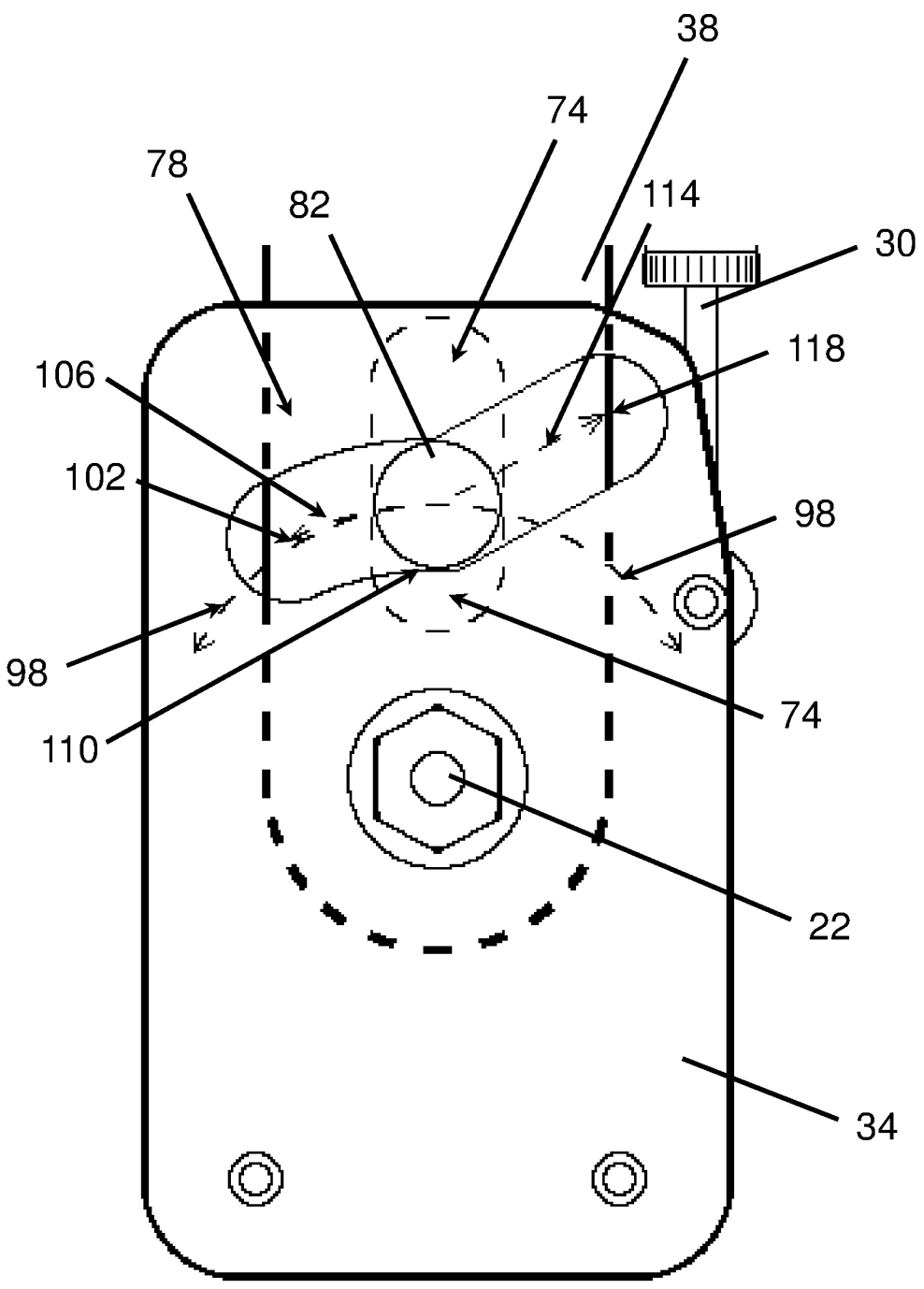
FIG. 3C shows another detailed side view drawing of the control joint.

FIG. 3C shows another detailed side view of the ankle motion control joint 20. The control joint 20 is the same as is shown in FIG. 3A except that the cam mechanism 26 has a differently shaped horizontal cam profile slot 78. The horizontal cam slot 78 includes a dorsiflexion end stop 102, a dorsiflexion travel zone 106, a neutral position 110, a plantarflexion travel zone 114, and a plantarflexion end stop 118. Compared to the horizontal cam profile slot shown in FIG. 3A or FIG. 3B, the dorsiflexion travel zone 106 maintains a smaller positive slope and is less steeply sloped away from the neutral position 110. The dorsiflexion travel zone 106 has a curved travel path which maintains a more constant slope that is about 2 degrees. The plantarflexion travel zone 114 is the same as shown in FIG. 3A.

Alternatively, a dorsiflexion travel zone 106 that has a negative slope and an inwardly curved path would allow the cam follower 82 to move downwardly during dorsiflexion and would provide an even stronger bias or force to lift the user's toes in dorsiflexion.

The neutral position 110 of the horizontal cam slot 78 includes a detent position which is slightly less sharp than that of FIG. 3A but still maintains a local minimum position for the cam follower 82 as well as a distinct change in direction/slope between the dorsiflexion travel zone 106 and the plantarflexion travel zone 114 at the neutral position 110. The cam profile slot 78 provides the same bias to move the foot from toes extended or pointed towards a neutral position as that of FIG. 3A and a stronger bias to move the foot from the neutral position and towards having the toes lifted than that of FIG. 3A or FIG. 3B.

Figure 3D:
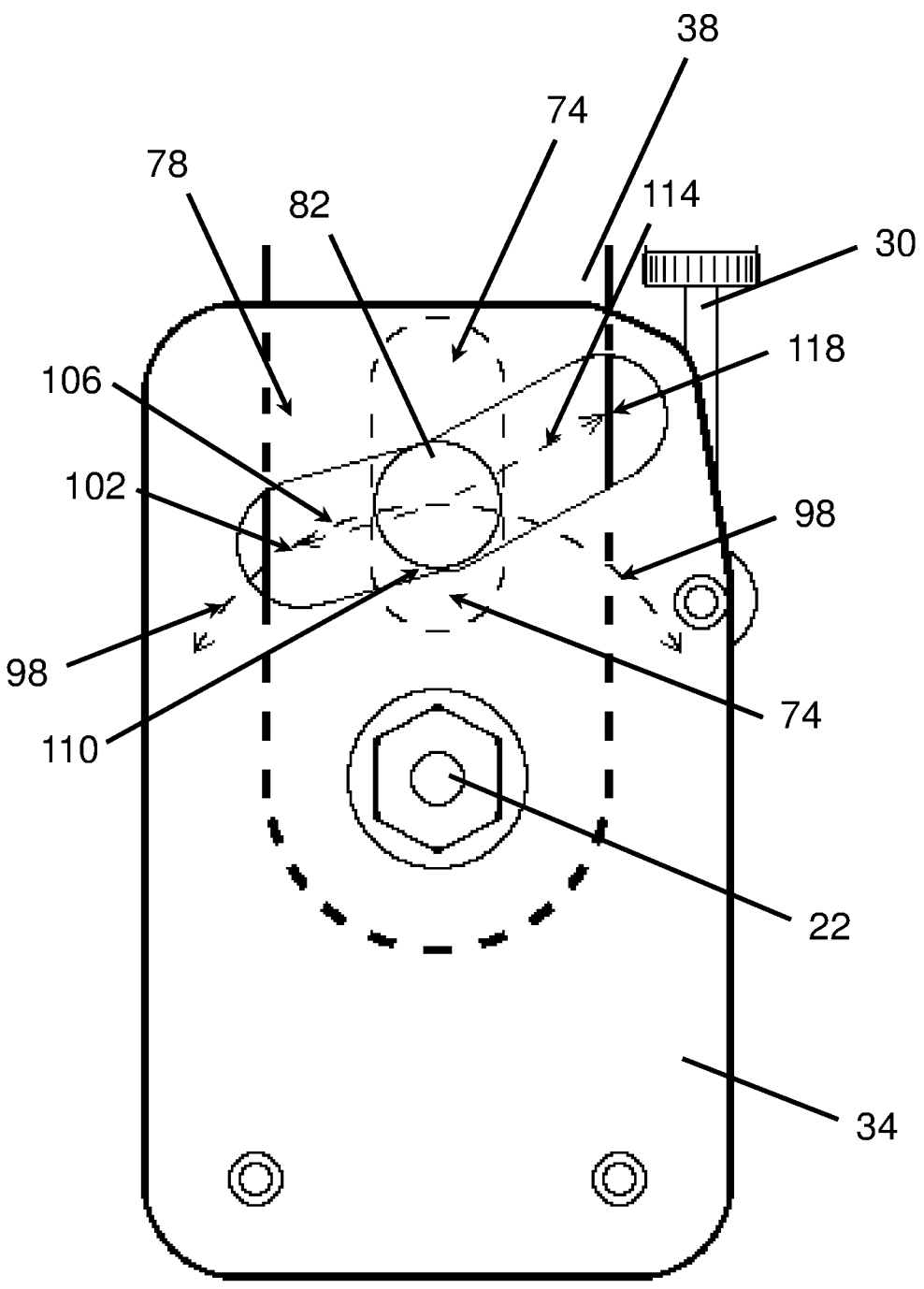
FIG. 3D shows another detailed side view drawing of the control joint.

FIG. 3D shows another detailed side view of the ankle motion control joint 20. The control joint 20 is the same as is shown in FIG. 3A except that the cam mechanism 26 has a differently shaped horizontal cam profile slot 78. The horizontal cam slot 78 includes a dorsiflexion end stop 102, a dorsiflexion travel zone 106, a neutral position 110, a plantarflexion travel zone 114, and a plantarflexion end stop 118. Compared to the horizontal cam profile slot shown in FIG. 3A or FIG. 3C, the dorsiflexion travel zone 106 maintains a smaller slope. The dorsiflexion travel zone 106 is straight but initially presents a negative slope and which then begins a positive slope about halfway through the dorsiflexion travel zone 106. This allows the cam follower 82 to move downwardly for the first have of travel towards the dorsiflexion end stop 102 and then gradually begin to move upwardly as motion continues towards the dorsiflexion end stop 102. The dorsiflexion travel zone 106 has a slope that initially is about negative 5 degrees, that transitions to zero slope near the middle of the travel zone 106, and then transitions to about positive 5 degrees near the dorsiflexion end stop 102. The plantarflexion travel zone 114 is the same as shown in FIG. 3A.

The neutral position 110 of the horizontal cam slot 78 does not present a local minimum position for the cam follower 82. The neutral position 110 does provide a change in slope between the dorsiflexion travel zone 106 and the plantarflexion travel zone 114, with the slope increasing as the foot motion control member 34 pivots from the dorsiflexion travel zone 106 into the plantarflexion travel zone 114. The cam profile slot 78 provides the same bias to move the foot from toes extended or pointed towards a neutral position as that of FIG. 3A and a stronger bias to move the foot from the neutral position and towards having the toes lifted than that of FIG. 3A, FIG. 3B, of FIG. 3C.

Figure 3E:
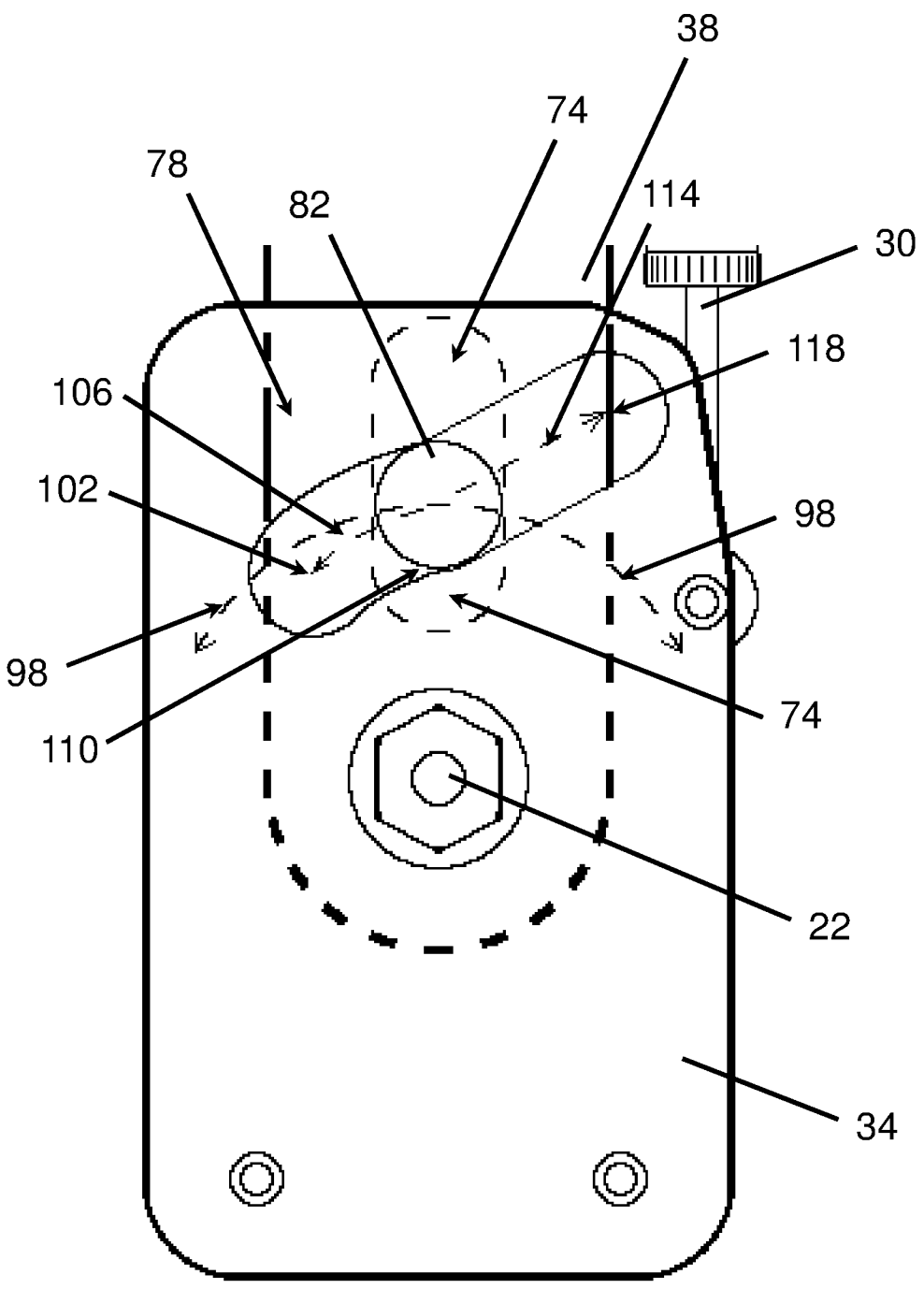
FIG. 3E shows another detailed side view drawing of the control joint.
Figure 3F:
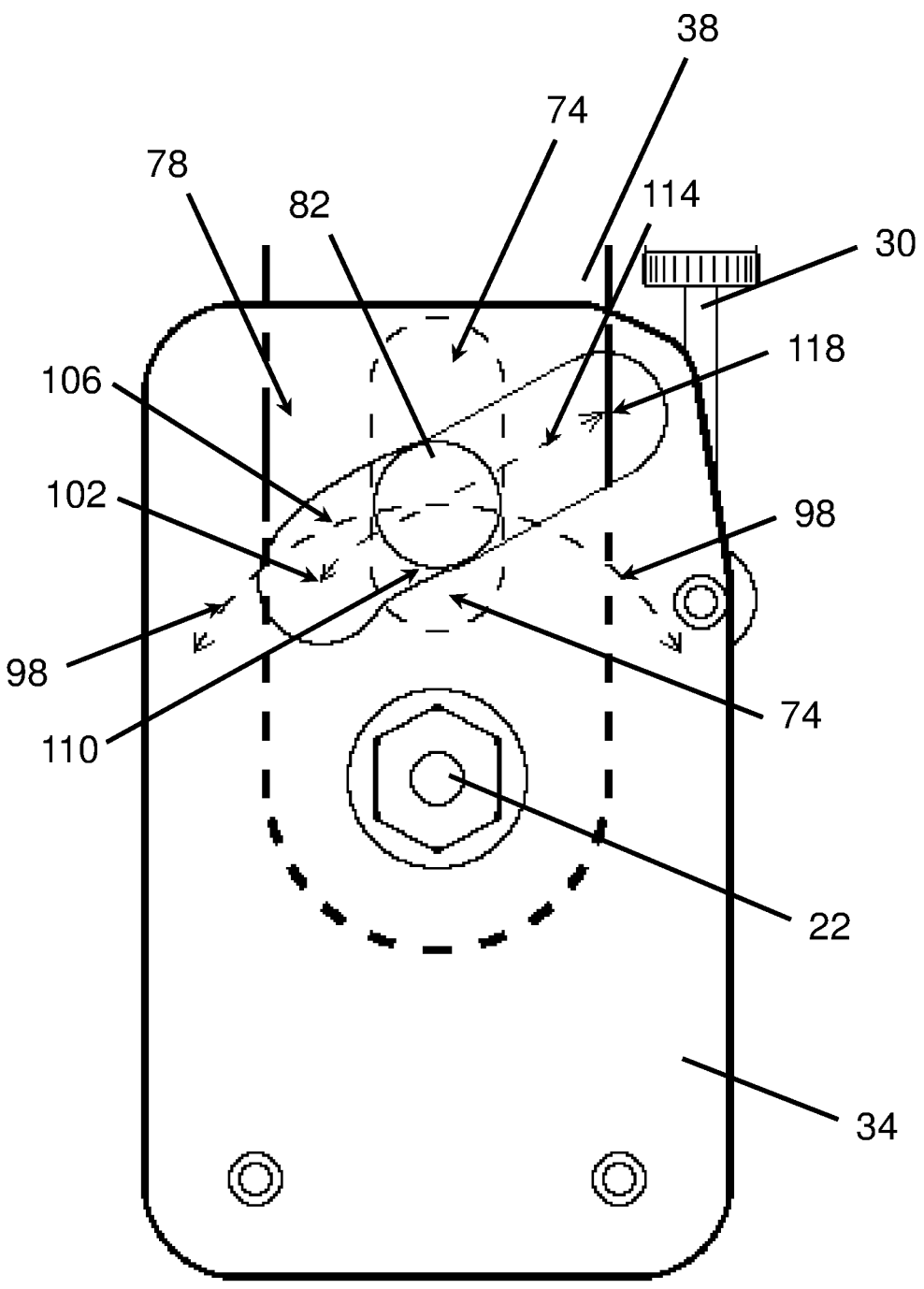
FIG. 3F shows another detailed side view drawing of the control joint.
Figure 3G:
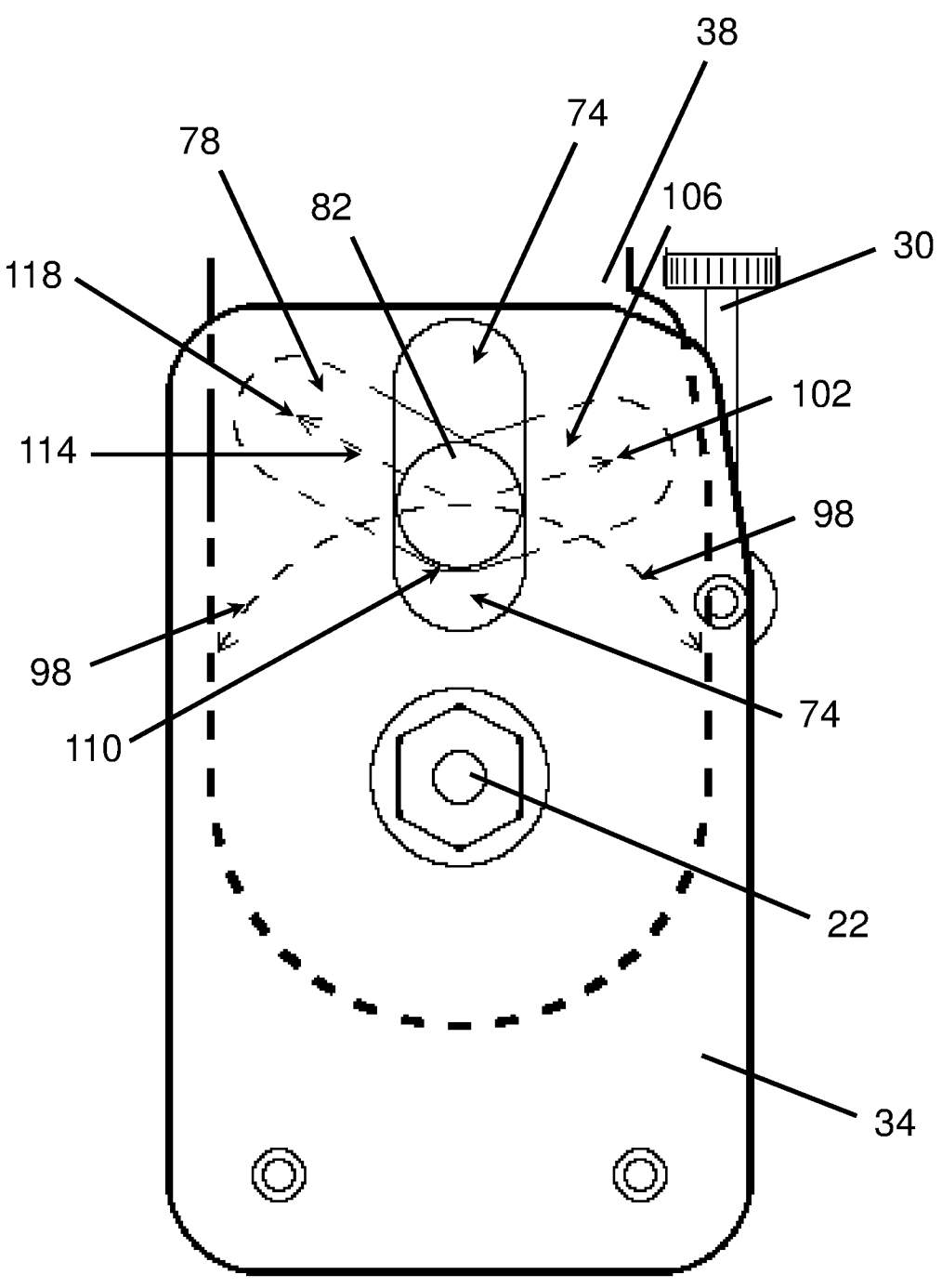
FIG. 3G shows another detailed side view drawing of the control joint.

FIG. 3E shows another detailed side view of the ankle motion control joint 20. The control joint 20 is the same as is shown in FIG. 3A except that the cam mechanism 26 has a differently shaped horizontal cam profile slot 78. The horizontal cam slot 78 includes a dorsiflexion end stop 102, a dorsiflexion travel zone 106, a neutral position 110, a plantarflexion travel zone 114, and a plantarflexion end stop 118. The dorsiflexion travel zone 106 has a downwardly curved path similar to that of FIG. 3C except that the dorsiflexion travel zone 106 maintains a smaller negative constant slope that is about negative 5 degrees. The plantarflexion travel zone 114 is the same as shown in FIG. 3A. The dorsiflexion travel zone 106 allows the cam follower 82 to move downwardly during dorsiflexion and provides a stronger bias or force to lift the user's toes in dorsiflexion.

The neutral position 110 of the horizontal cam slot 78 does not provide a local minimum position for the cam follower 82 but does provide a small change in direction/slope between the dorsiflexion travel zone 106 and the plantarflexion travel zone 114 at the neutral position 110. The cam profile slot 78 provides the same bias to move the foot from toes extended or pointed towards a neutral position as that of FIG. 3A and a stronger bias to move the foot from the neutral position and towards having the toes lifted than that of FIG. 3A, FIG. 3B, or FIG. 3C.

FIG. 3F shows another detailed side view of the ankle motion control joint 20. The control joint 20 is the same as is shown in FIG. 3A except that the cam mechanism 26 has a differently shaped horizontal cam profile slot 78. The horizontal cam slot 78 includes a dorsiflexion end stop 102, a dorsiflexion travel zone 106, a neutral position 110, a plantarflexion travel zone 114, and a plantarflexion end stop 118. The dorsiflexion travel zone 106 has a downwardly curved path similar to that of FIG. 3E except that the dorsiflexion travel zone 106 provides an increasingly negative slope that begins at about negative 10 degrees and increases to about negative 20 degrees. The plantarflexion travel zone 114 is the same as shown in FIG. 3A. The dorsiflexion travel zone 106 allows the cam follower 82 to move downwardly during dorsiflexion and provides a stronger bias or force to lift the user's toes in dorsiflexion as the foot support 18 and foot motion control member 34 near the end of travel in dorsiflexion.

The neutral position 110 of the horizontal cam slot 78 does not provide a local minimum position for the cam follower 82 but does provide a small change in direction/slope between the dorsiflexion travel zone 106 and the plantarflexion travel zone 114 at the neutral position 110. The cam profile slot 78 provides the same bias to move the foot from toes extended or pointed towards a neutral position as that of FIG. 3A and a stronger bias to move the foot from the neutral position and towards having the toes lifted than that of FIG. 3A, FIG. 3B, or FIG. 3C.

The horizontal cam profile slots 78 of FIGS. 3A, 3b, and 3C provide a stronger detent or stabilizing force at the neutral position 110 and thereby provide a stronger stabilizing force to help a person stand without losing control over their foot and their balance. The horizontal cam profile slots 78 of FIGS. 3D, 3E, and 3F help a person with a more severely reduced ability to lift their foot in dorsiflexion and provide a stronger lifting force to the foot while lifting the foot for walking to help the person avoid dragging the foot while walking.

Figure 4:
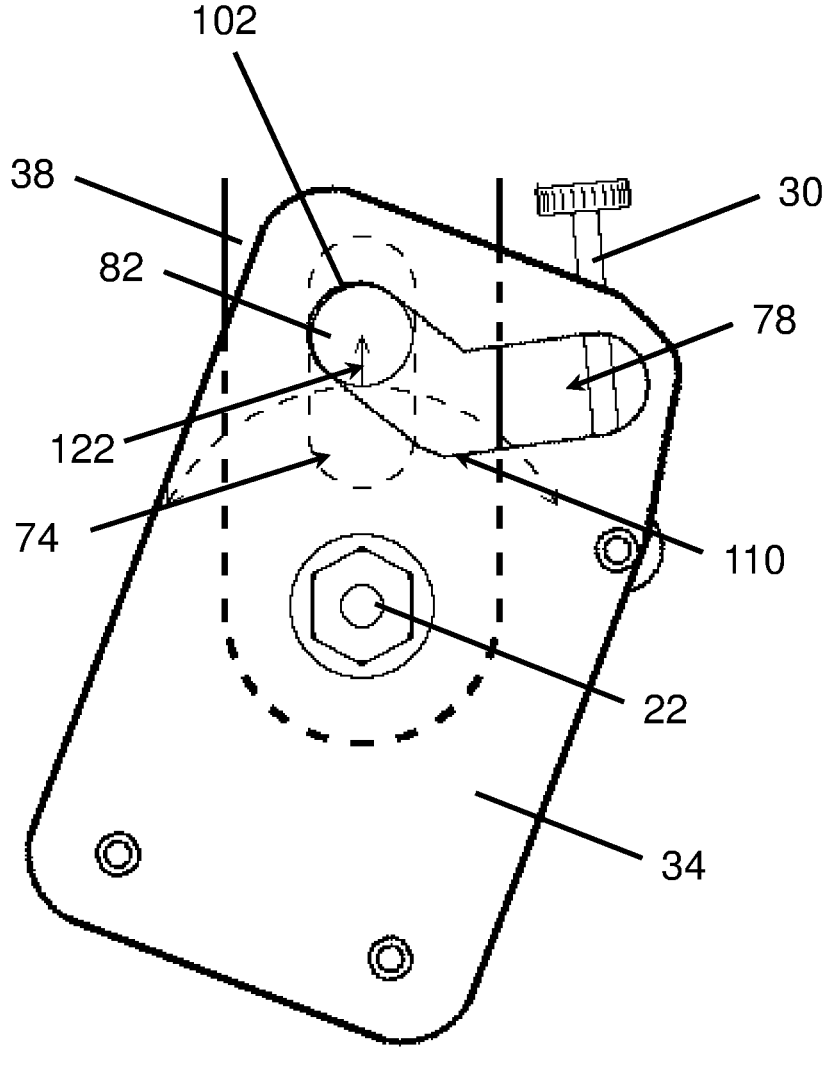
FIG. 4 shows another detailed side view drawing of the control joint.

FIG. 4 shows the control joint 20 of FIG. 3A with the foot support 18 and foot control joint member 34 pivoted in dorsiflexion to lift the user's toes. The cam follower 82 has moved vertically within the vertically oriented cam slot 74 a smaller distance as indicated by arrow 122. The cam follower has moved to the dorsiflexion end stop 102, preventing further rotation of the foot motion control member 34 and the user's foot. The neutral detent position 110 is more easily seen. FIG. 4 also illustrates how the spring strut 30 extends as the foot control joint member 34 rotates in dorsiflexion. As configured, the spring strut 30 provides an extension force and biases the foot control member 34 to pivot in dorsiflexion as shown.

Figure 5:
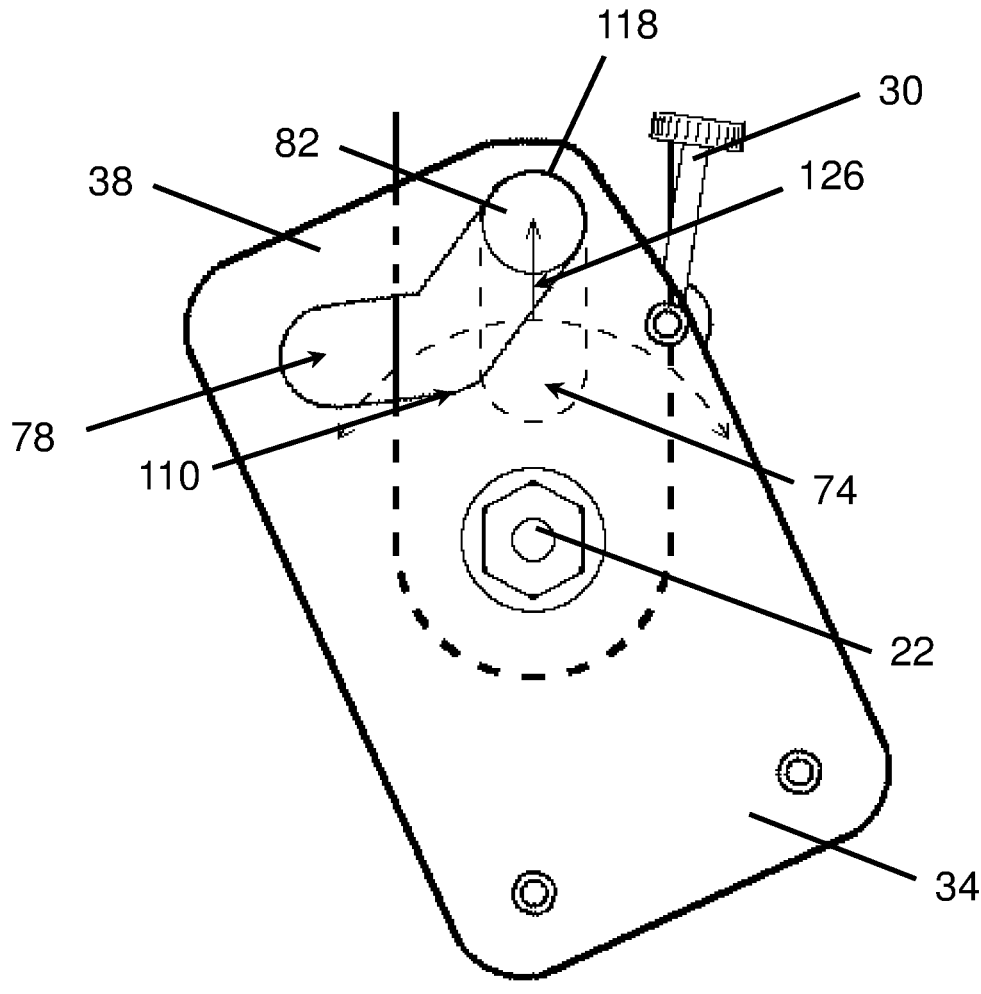
FIG. 5 shows another detailed side view drawing of the control joint.

FIG. 5 similarly shows the control joint 20 of FIG. 3A with the foot brace and foot control joint member 34 pivoted in plantarflexion to point the user's toes. The cam follower 82 has moved vertically within the vertically oriented cam slot 74 a greater distance than that of FIG. 4 as indicated by arrow 126. The cam follower has moved to the plantarflexion end stop 118 and prevents further rotation of the foot motion control member 34 and the user's foot. FIG. 5 also illustrates how the spring strut 30 is compressed as the foot control joint member 34 rotates in plantarflexion. As configured, the spring strut 30 provides an extension force and resists the pivoting of the foot control member 34 in plantarflexion as shown.

Figure 6:
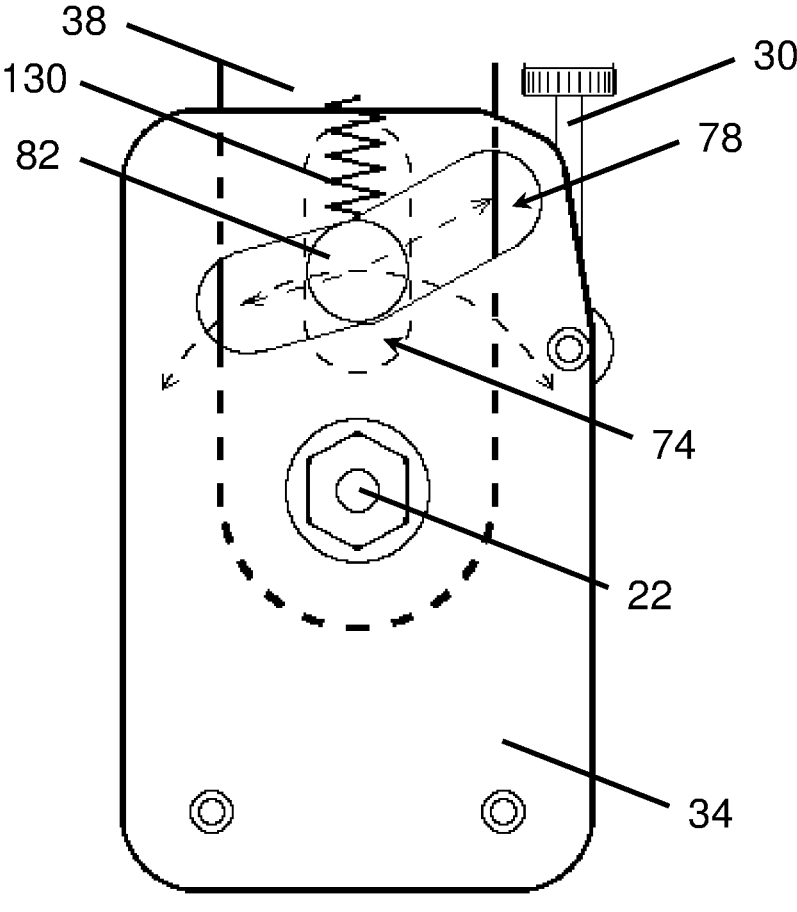
FIG. 6 shows another detailed side view drawing of the control joint.

FIG. 6 shows the control joint with an additional cam spring 130 which is attached to the leg control joint member 38 and which biases the cam follower 82 towards the pivot point 22. The spring 130 may provide some additional resistance to movement of the cam follower 82 away from the pivot joint 22. For horizontal cam profile slots 78 such as FIGS. 3A, 3B, and 3C with a neutral position 110 that provides a local minimum for the cam follower position within the vertical cam slot 74, the spring 130 increases the stabilizing force against rotation at the neutral position and also increases the resistance to rotation away from the neutral position through the dorsiflexion travel zone 106 and the plantarflexion travel zone 114 according to the slope of either travel zone. For the example embodiment of FIG. 3C, the spring 130 provides little resistance to movement along the dorsiflexion travel zone 106, increases the stabilizing force at the neutral position, and increases resistance to plantarflexion pivoting in the plantarflexion travel zone 114. For horizontal cam profile slots 78 such as those in FIGS. 3D, 3E, and 3F that do not have a local minimum for the cam follower 82 at the neutral position, the spring 130 assists the force applied by spring strut 30 but does not significantly change the balance of rotational force resistance applied to the foot control joint member 34 between dorsiflexion and plantarflexion. For the horizontal cam profile slot 78 shown in FIG. 3D, the spring 130 would urge the foot control joint member 34 to rotate in dorsiflexion about halfway to the dorsiflexion end stop 102 and would then oppose further rotation of the foot control joint member 34 towards the dorsiflexion end stop 102.

Figure 7:
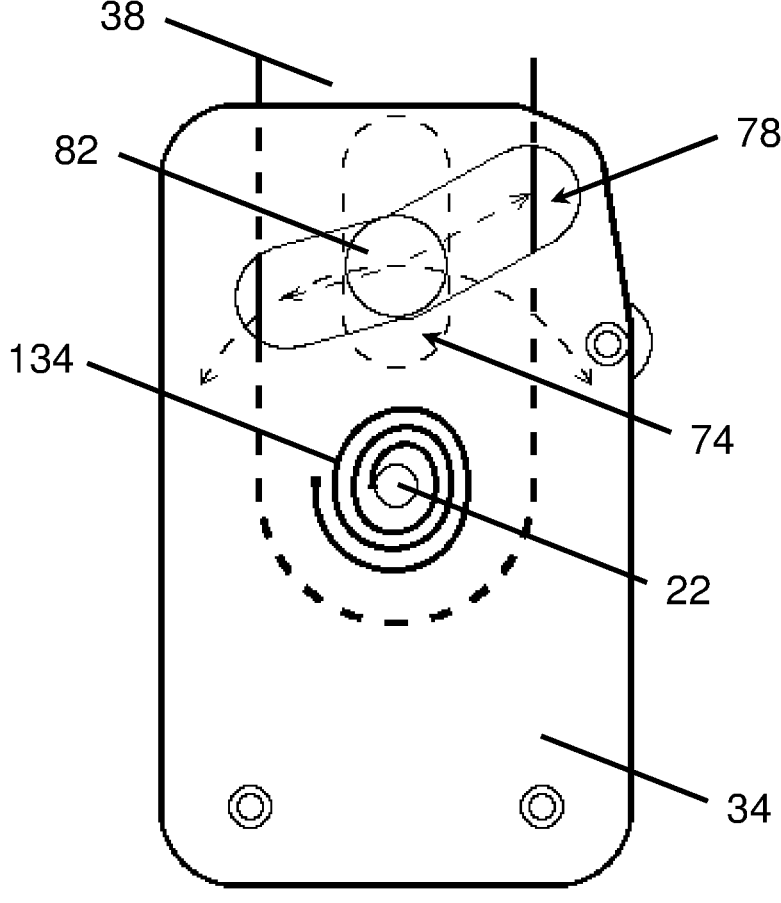
FIG. 7 shows another detailed side view drawing of the control joint.

FIG. 7 shows the control joint with a coil spring 134 disposed around the pivot joint 22 and connected to the foot control joint member 34 and the leg control joint member 38 so as to bias the foot brace 18 and foot control joint member 34 into dorsiflexion. A torsion spring 134 may replace the linear spring strut 30.

The spring strut 30 will naturally urge the foot control joint member 34 and the foot support 18 in dorsiflexion to a position where the user's toes are lifted upwardly. This causes or assists the user's foot/toes to lift when weight is removed from the foot; addressing a drop foot condition caused by nerve or muscle impairment. As the user puts weight on the foot, the strut 30 is compressed to allow the foot to come to a neutral position. The strut 30 may further include internal fluid and a damping piston which slows and dampens the movement of the foot.

As the foot control joint member 34 and the foot support 18 pivot relative to the leg control joint member 38, the shaped horizontal cam profile slot 78 forces the cam follower 82 to move vertically within the vertical cam slot 74. This motion is impeded by a spring acting upon the cam follower 82 or by gravity acting upon the cam follower 82 and also by friction acting upon the cam follower 82. The shaped horizontal cam slot 78 may be designed with a generally horizontal portion or a detent position at the neutral position of the foot brace 18 to provide a local minimum for the cam follower at the neutral position 110. The dorsiflexion travel zone 106 and plantarflexion travel zone 114 may curve, progressively increasing or decreasing their slope relative to neutral to thereby create a more progressive resistance to motion or assistance to motion. The ends of the arcuate cam slot 78 provide stops 102, 118 which limit the range of motion of the foot brace 18 and foot. The device 10 may limit the range of motion in pivoting the foot in dorsiflexion and plantarflexion to a range that is less than that of the natural foot to thereby assist a person that otherwise has difficulty in controlling their foot. As the foot is pivoted at the ankle between dorsiflexion and plantarflexion, the movement of the cam follower in the vertical slot may be relatively small; resulting in smaller resistance to small movements. As the foot is pivoted farther away from neutral, the arcuate cam slot 78 may increase in slope from horizontal and cause greater vertical movements of the cam follower 82 in the vertical cam slot 74. As the involved section of the arcuate horizontal cam slot 78 becomes closer to parallel to the vertical cam slot 74, the force required to move the cam follower 82 upwardly increases and thus resistance to further pivoting of the foot brace 18 increases. The cam follower 82 thus provides a limit to the range of motion of the foot brace 18 and resistance to motion with less resistance around a neutral position 110 where a user may have greater control over their foot and greater resistance to motion at more extreme foot positions where a user may have less control over moving their foot. The spring strut 30 also provides resistance to motion as well as biasing the foot brace 18 to pivot in dorsiflexion to address a drop foot condition.

The device assists a user in all stages of walking to achieve better controlled foot movement and increased stability. When a person has nerve or muscle impairment that affects control over their foot, they may have insufficient strength or control over their foot through the walking gait cycle. The device biases the foot in dorsiflexion to pull the toe up. This helps a user to avoid striking the front of their foot and helps them to not trip while walking. The device also slows and controls the movement of the foot. The movement of the cam follower 82 through the vertical cam slot 74 and horizontal cam slot 78 causes sufficient friction to limit fast foot movements without causing undue resistance to movement at a desired foot speed while walking.

This prevents uncontrolled quick movement of the foot, such as quick movement of the front of the foot downwardly after heel strike while walking. Uncontrolled foot movement while walking often causes the front of the foot to quickly slap the ground after heel strike. The device limits the speed of foot movement and prevents uncontrolled foot slap or other undesired movements. The device also increases the user's control over their waking gait by adding resistance and slowing the motion of the foot in the downward motion of the foot after heel strike, towards a neutral standing position and through dorsiflexion as the user places weight on their toes. The device also aids the user in pushing off of the toe. The resistance to quick motion created by the cam and cam follower assists the user in pushing off with their toes. Once the user has pushed off of their toes and is not putting weight on the motion control joint, the device is able to move more quickly and assists in lifting the toes to avoid toe strike.

The device 10 provides additional control over the position of the foot and adds stability to the foot and ankle while still allowing sufficient ankle flexion for walking and normal activities. The device 10 allows a person with nerve or muscle damage which affects their foot and ankle to stand and walk with greater ease and without placing strain on surrounding body parts as a result of compensating for the weakened foot/ankle. The person is able to perform daily tasks and participate in activities which were not previously possible.

The above description of illustrated examples of the present invention, including what is described in the Abstract, is not intended to be exhaustive or to be limiting to the precise forms disclosed. While specific examples of the invention are described herein for illustrative purposes, various equivalent modifications are possible without departing from the broader scope of the present claims. Indeed, it is appreciated that specific example dimensions, materials, etc., are provided for explanation purposes and that other values may also be employed in other examples in accordance with the teachings of the present invention.

What is claimed is:

1. An ankle and foot orthotic device comprising:
a leg support shell configured for attachment to a user's lower leg;
a leg control joint member that extends downwardly from the leg support shell, wherein the leg control joint member comprises a lower end that is positioned adjacent a user's ankle when the device is in use;
a foot support configured for attachment to an underside of a user's foot to support the user's foot;
a foot control joint member that extends upwardly from the foot support, wherein the foot control joint member comprises an upper end that is positioned adjacent the leg control joint member lower end;
a motion control joint connecting the foot control joint member to the leg control joint member comprising:
a pivot joint connecting the foot control joint member to the leg control joint member and providing for pivotal motion between the foot control joint member and the leg control joint member, wherein the pivot joint is aligned with a user's ankle when the device is in use;
a biasing member which biases a distal, toe end of the foot support upwardly towards the leg support shell in dorsiflexion;
a control cam comprising:

a vertically oriented cam slot disposed in one of the foot control joint member and the leg control joint member;
a horizontally oriented cam profile slot disposed in the other of the foot control joint member and the leg control joint member, the horizontally oriented cam profile slot comprising;
a neutral position;
a dorsiflexion travel zone;
a dorsiflexion end stop;
a plantarflexion travel zone;
a plantarflexion end stop;
a cam follower disposed to engage both the vertically oriented cam slot and the horizontally oriented profile cam slot; and
wherein pivoting the foot control joint member relative to the leg control joint member about the pivot joint causes the cam follower to move vertically within the vertically oriented cam slot and to move to a different position within the horizontally oriented cam profile slot.

2. The device of claim 1, wherein the vertically oriented cam slot is formed in the leg control joint member, and wherein the horizontally oriented cam profile slot is formed in the foot control joint member.

3. The device of claim 1, wherein the dorsiflexion travel zone has a positive slope away from the neutral position such that pivoting the foot support away from the neutral position in dorsiflexion causes the cam follower to move upwardly in the vertical cam slot and wherein the plantarflexion travel zone has a positive slope away from the neutral position such that pivoting the foot support away from the neutral position in plantarflexion causes the cam follower to move upwardly in the vertically oriented cam slot.

4. The device of claim 3, wherein the plantarflexion travel zone slope is greater than the dorsiflexion travel zone slope.

5. The device of claim 3, wherein the neutral position comprises a detent wherein the cam follower is located at a minimum height in the vertically oriented cam slot.

6. The device of claim 1, wherein the dorsiflexion travel zone has a negative slope away from the neutral position such that pivoting the foot support away from the neutral position in dorsiflexion causes the cam follower to move downwardly in the vertically oriented cam slot and wherein the plantarflexion travel zone has a positive slope away from the neutral position such that pivoting the foot support away from the neutral position in plantarflexion causes the cam follower to move upwardly in the vertically oriented cam slot.

7. The device of claim 1, wherein the leg support shell is shaped to engage a front shin area of a lower leg.

8. The device of claim 1, wherein the foot support is shaped to receive a bottom of a foot and wherein the foot support is shaped to extend around a heel and extend forward to a position adjacent the ball of a foot and to terminate before toes of the foot.

9. An ankle and foot orthotic device comprising:
a leg support shell configured for attachment to a user's lower leg;
a foot support configured for attachment to an underside of a user's foot to support the user's foot;
a motion control joint formed between a first control joint member and a second control joint member and connecting the foot support to the leg support shell comprising:

a pivot joint which provides pivotal motion between the foot support and the leg support shell to thereby pivot a front of the foot support upwards and downwards towards and away from the leg support shell;

a biasing member which biases a distal, toe end of the foot support upwardly towards the leg shell in dorsiflexion; and a control cam comprising:
a vertically oriented cam slot disposed in the first control joint member;
a horizontally oriented cam profile slot disposed in the second control joint member, the horizontally oriented cam profile slot comprising;
a neutral position;
a dorsiflexion travel zone;
a dorsiflexion end stop;
a plantarflexion travel zone;
a plantarflexion end stop;
a cam follower disposed to engage both the vertically oriented cam slot and the horizontally oriented cam profile slot and to move within the vertically oriented cam slot and the horizontally oriented cam profile slot; and wherein pivoting the first control joint member relative to the second control joint member about the pivot joint causes the cam follower to move vertically within the vertically oriented cam slot and to move to a different position within the horizontally oriented cam profile slot.

10. The device of claim 9, wherein the first control joint member comprises a leg control joint member that extends downwardly from the leg support shell, and wherein the leg control joint member comprises a lower end that is positioned adjacent a user's ankle when the device is in use, and wherein the second control joint member comprises a foot control joint member that extends upwardly from the foot support, and wherein the foot control joint member comprises an upper end that is positioned adjacent the leg control joint member lower end.

11. The device of claim 9, wherein the dorsiflexion travel zone has a positive slope away from the neutral position such that pivoting the foot support away from the neutral position in dorsiflexion causes the cam follower to move upwardly in the vertically oriented cam slot and wherein the plantarflexion travel zone has a positive slope away from the neutral position such that pivoting the foot support away from the neutral position in plantarflexion causes the cam follower to move upwardly in the vertically oriented cam slot.

12. The device of claim 11, wherein the plantarflexion travel zone slope is greater than the dorsiflexion travel zone slope.

13. The device of claim 11, wherein the neutral position comprises a detent wherein the cam follower is located at a minimum height in the vertically oriented cam slot.

14. The device of claim 11, wherein the control cam resists pivoting of the foot support away from the neutral position in dorsiflexion, and wherein the biasing member promotes pivoting of the foot support away from the neutral position in dorsiflexion such that overall the foot support is biased away from the neutral position in dorsiflexion.

15. The device of claim 9, wherein the dorsiflexion travel zone has a negative slope away from the neutral position such that pivoting the foot support away from the neutral position in dorsiflexion causes the cam follower to move downwardly in the vertically oriented cam slot and wherein the plantarflexion travel zone has a positive slope away from the neutral position such that pivoting the foot support away from the neutral position in plantarflexion causes the cam follower to move upwardly in the vertically oriented cam slot.

16. An ankle and foot orthotic device comprising:
a leg support configured for attachment to a user's lower leg;
a foot support configured for attachment to a user's foot;
a motion control joint formed between a first control joint member and a second control joint member and connecting the foot support to the leg support comprising:
a pivot joint which provides pivotal motion between the foot support and the leg support to thereby pivot a front of the foot support upwards and downwards towards and away from the leg support;
a biasing member which biases a distal, toe end of the foot support upwardly towards the leg shell in dorsiflexion; and
a control cam comprising:
a vertically oriented cam slot disposed in the first control joint member;
a horizontally oriented cam profile slot disposed in the second control joint member, the horizontally oriented cam profile slot comprising;
a neutral position;
a dorsiflexion travel zone;
a dorsiflexion end stop;
a plantarflexion travel zone;
a plantarflexion end stop;
a cam follower disposed to engage both the vertically oriented cam slot and the horizontally oriented cam profile slot and to move within the vertically oriented cam slot and the horizontally oriented cam profile slot; and wherein pivoting the first control joint member relative to the second control joint member about the pivot joint causes the cam follower to move vertically within the vertically oriented cam slot and to move to a different position within the horizontally oriented cam profile slot.

17. The device of claim 16, wherein the first control joint member comprises a leg control joint member that extends downwardly from the leg support shell, and wherein the leg control joint member comprises a lower end that is positioned adjacent a user's ankle when the device is in use, and wherein the second control joint member comprises a foot control joint member that extends upwardly from the foot support, and wherein the foot control joint member comprises an upper end that is positioned adjacent the leg control joint member lower end.

18. The device of claim 16, wherein the dorsiflexion travel zone has a positive slope away from the neutral position such that pivoting the foot support away from the neutral position in dorsiflexion causes the cam follower to move upwardly in the vertically oriented cam slot and wherein the plantarflexion travel zone has a positive slope away from the neutral position such that pivoting the foot support away from the neutral position in plantarflexion causes the cam follower to move upwardly in the vertically oriented cam slot.

19. The device of claim 18, wherein the control cam resists pivoting of the foot support away from the neutral position in dorsiflexion, and wherein the biasing member promotes pivoting of the foot support away from the neutral position in dorsiflexion such that overall the foot support is biased away from the neutral position in dorsiflexion.

20. The device of claim 16, wherein the dorsiflexion travel zone has a negative slope away from the neutral position such that pivoting the foot support away from the neutral position in dorsiflexion causes the cam follower to move downwardly in the vertically oriented cam slot and wherein the plantarflexion travel zone has a positive slope away from the neutral position such that pivoting the foot support away from the neutral position in plantarflexion causes the cam follower to move upwardly in the vertically oriented cam slot.

* * * * *